(12) United States Patent
Chen et al.

(10) Patent No.: US 11,866,413 B2
(45) Date of Patent: Jan. 9, 2024

(54) COMPOSITION OF 5-FLUOROURACIL AND REFINING METHOD THEREFOR

(71) Applicant: SHANGHAI XUDONG HAIPU PHARMACEUTICAL CO., LTD, Shanghai (CN)

(72) Inventors: Xiaolin Chen, Shanghai (CN); Pengfei Gao, Shanghai (CN); Yike Yang, Shanghai (CN); Yi Liang, Shanghai (CN); Yafeng Zhan, Shanghai (CN)

(73) Assignee: SHANGHAI XUDONG HAIPU PHARMACEUTICAL CO., LTD, Shanghai (CN)

( * ) Notice: Subject to any disclaimer, the term of this patent is extended or adjusted under 35 U.S.C. 154(b) by 0 days.

(21) Appl. No.: 17/629,777

(22) PCT Filed: Jan. 10, 2020

(86) PCT No.: PCT/CN2020/071350
§ 371 (c)(1),
(2) Date: Jan. 24, 2022

(87) PCT Pub. No.: WO2021/022788
PCT Pub. Date: Feb. 11, 2021

(65) Prior Publication Data
US 2022/0348548 A1    Nov. 3, 2022

(30) Foreign Application Priority Data
Aug. 5, 2019 (CN) .......................... 201910716013.1

(51) Int. Cl.
*C07D 239/553* (2006.01)
(52) U.S. Cl.
CPC ................ *C07D 239/553* (2013.01)
(58) Field of Classification Search
CPC .................................. C07D 239/553
See application file for complete search history.

(56) References Cited

FOREIGN PATENT DOCUMENTS

| CN | 104447576 A | 3/2015 |
|---|---|---|
| CN | 107963994 A | 4/2018 |
| WO | 2005089511 A2 | 9/2005 |

OTHER PUBLICATIONS

Pasha et al., Stability indicating analytical method development, validation, method transfer and impurity profile (related substances) of 2,4-dihydroxy-5-fluoropyrimidine by liquid chromatography, International Journal of Pharmaceutical Research and Applications, vol. 1, issue 1, pp. 53-59 (Oct. 2016).*
Prabu et al., Impurities and its importance in pharmacy, International Journal of Pharmaceutical Schiences Review and Research, vol. 3, Issue 2, pp. 66-71 (Aug. 2010).*
Javadzadeh et al., Recrystallization of Drugs: Significance on pharmaceutical processing, Recrystallization, Publisher: InTech, Chapter 18, pp. 425-446 (2012).*
May 9, 2020 International Search Report issued in International Patent Application No. PCT/CN2020/071350.
May 9, 2020 Written Opinion of the International Searching Authority issued in International Patent Application No. PCT/CN2020/071350.
D. H. R. Barton et al., A Convenient Synthesis of 5-Fluorouracil, The Journal of Organic Chemistry, Jan. 1, 1972, pp. 329-330, vol. 37, No. 2.
Li, Zhenghua, Fluorouracil, Medicinal Chemistry, 2nd edition, Nov. 30, 1979, pp. 328-329, Xinhua Bookstore Beijing, CN.

* cited by examiner

*Primary Examiner* — Deepak R Rao (57) ABSTRACT

Disclosed is a method for refining 5-fluorouracil, comprising the following steps: dissolving 5-fluorouracil in an organic solvent, preferably DMSO, heating and stirring until dissolved; naturally cooling the filtrate until a crystal is precipitated; filtering, washing a filter cake using a polar solvent, and draining and drying under reduced pressure. By using the new refining method, the content of impurities in 5-fluorouracil may be reduced to less than 0.01%, the product purity is more than 99.98%, and the refining yield is higher than 70%. In addition, the refining method of the present invention has a simple process, convenient operation, low production costs, high product purity, a stable process, and is suitable for industrial production.

13 Claims, 5 Drawing Sheets

COMPOSITION OF 5-FLUOROURACIL AND REFINING METHOD THEREFOR

TECHNICAL FIELD

The present disclosure belongs to the technical field of medicines, and particularly relates to a refining method for a 5-fluorouracil related substance and a composition thereof.

BACKGROUND 5-fluorouracil (5-Fu, chemical name 5-fluoro-2,4(1H, 3H)-pyrimidinedione, shown in Compound I) is first prepared by Duschinsky et al in 1957, and launched in the United States in 1962. It is an important anti-tumor drug. As an anti-metabolite anti-tumor drug, it may be used for the treatment of various cancers and is a clinical first-line chemotherapy drug. 5-fluorouracil has a good clinical effect in the treatment of tumors, and it attracts the attention of major pharmaceutical companies at present. The quality of a 5-fluorouracil refined product is also the key to affecting a fluorouracil active pharmaceutical ingredient.

Compound I

5-Fu

5-fluorouracil is not only an important anti-tumor drug, but also a key intermediate for preparation of capecitabine and other anti-tumor drugs, so the 5-fluorouracil active pharmaceutical ingredient has a broad market prospect.

At present, there are several ways to synthesize 5-fluorouracil:

Direct fluorination method: after a reaction of elemental fluorine and organic compound is widely researched in the 1970s, a method of direct fluorination to prepare 5-fluorine also emerges. This method mainly uses uracil, cytosine, orotic acid and the like as raw materials, and uses $F_2$ diluted with an inert gas ($N_2$, He) or an active-type fluorine-containing compound ($SF_6$, $CF_3OF$, $FOSO_2F$, $C_{19}XeF_6$, $CsSO_4F$ and the like) as a fluorine source, which may be reacted in an acidic solvent to generate a corresponding intermediate, and 5-Fu may be obtained after post-treatment. Although this method is simple, it is not widely used in China due to the expensive price of the fluorine gas or the use of the corrosive or toxic fluorine source.

Condensation cyclization method: this method is the earliest method for synthesizing 5-fluorouracil, and it is also the synthesis method adopted by most of manufacturers for producing fluorouracil in China at present. There are many routes for this method. After the continuous optimization, a more mature route is shown as follows:

Methyl fluoroacetate is used as a raw material, it is condensed with ethyl formate in toluene solution of sodium methoxide to obtain a fluoroformyl acetate enol sodium salt. This intermediate is directly cyclized with O-methylisourea sulfate without separation to obtain 2-methoxy-5-fluorouracil, and then it is hydrolyzed into 5-fluorouracil in a dilute hydrochloric acid. This route has many advantages such as low cost and easy availability of raw materials, simple and mild reaction conditions, and no need for a column chromatography, so it is adopted by most domestic enterprises, and is widely used in China. Other methods start from a derivative of a nitrogen-containing heterocycle, especially a pyrimidine ring, the raw materials are difficult to available, and it is not suitable for industrial production.

There are many impurities in the 5-fluorouracil active pharmaceutical ingredient prepared by the above method, its physical and chemical properties are very close to a finished product, and it is more difficult to remove these impurities, so the quality standards for the 5-fluorouracil active pharmaceutical ingredient adopted in various countries are all the lower standards, for example: Chinese Pharmacopoeia 2015 edition, Page 715, a regulation for a related substance in 5-fluorouracil is that the content of an individual impurity is less than 0.5%, and the total impurities are less than 0.75%; and European Pharmacopeia 9.2, a regulation for a related substance in 5-fluorouracil is that an individual impurity is less than 0.1% and total impurities are less than 0.5%. After an exhaustive literature search, it is found that most of literatures are about synthesis routes of fluorouracil, but there are few reports about its refining method. For example, it is reported in patent application CN10796399A that the purity reaches 99.82%, but a product still contains 0.18% of impurities; and especially dihydropyrimidine-2,4,5(3H)-tri-one (hereinafter referred to as an impurity B) and 5-methoxyuracil (hereinafter referred to as an impurity D), these two impurities are difficult to remove, the structures of the impurity B and the impurity D are respectively as follows:

Many drug candidates fail in trials due to unpredictable effects or toxicity of unwanted impurities on human metabolism, so it is very important to eliminate such impurities in the early stage of research and development, namely an active pharmaceutical ingredient stage.

With the increasingly strict and clear requirements for impurity researches in drug research and development in our country, especially the researches on drug by-products, degradation products and the like already enter a new stage today, whether a drug may generate adverse reactions in clinical use is increasingly important. Certainly, it is also clearly known that in the actual clinical field, the adverse reactions of the drug during the clinical use are not only related to the pharmacological activity of main components of the drug, but also related to related substances existing in the drug. Therefore, the purification of the related substances in 5-fluorouracil becomes the research emphasis.

In view of the shortages existing in the prior art, the present patent application provides a method for refining 5-fluorouracil which has a simple process, convenient operation, low production costs, high product purity, a stable process, and is suitable for industrial production.

Content of the Present Invention

A first aspect of the present disclosure provides a 5-fluorouracil raw material or active pharmaceutical ingredient, it contains 5-fluorouracil with a weight percentage of more than 99.9% and impurities with a weight percentage of less than 0.05%, and the impurities are selected from 5-methoxyuracil, and dihydropyrimidine-2,4,5(3H)-trione;

preferably, the weight percentage of the 5-methoxyuracil is 0.05% or less, preferably 0.02% or less, and further preferably 0.01% or less;

and/or, the weight percentage of the dihydropyrimidine-2,4,5(3H)-trione is 0.05% or less, preferably 0.02% or less, and further preferably 0.01% or less;

herein the structure of the 5-methoxyuracil is (D)

and the structure of the dihydropyrimidine-2,4,5(3H)-trione is (B)

Further, a composition prepared from the above raw material or active pharmaceutical ingredient.

Second aspect of the present disclosure: a refining method for high-purity 5-fluorouracil is provided, and it includes the following steps:

(i) the first step is heating and dissolving, dissolving 5-fluorouracil in an organic solvent, heating and stirring until dissolved;

(ii) the second step is cooling and crystallizing, naturally cooling filtrate until a crystal is precipitated; and (iii) the third step is filtering and drying, filtering, washing a filter cake by using water, and draining and drying under a reduced pressure.

Preferably, the organic solvent in the step (i) is dimethylsulfoxide.

Preferably, the mass ratio of the 5-fluorouracil to the dimethylsulfoxide in the step (i) is 1:2-6, further preferably 1:2.75-5.5, and further more preferably 1:3.3.

Preferably, the heating and dissolving temperature in the step (i) is 45° C.-80° C.

Preferably, the cooling and crystallizing temperature in the step (ii) is 5-15° C., and the crystallizing time is 5-12 hours.

Further, the impurities removed by the refining method includes:

5-methoxyuracil and/or dihydropyrimidine-2,4,5(3H)-trione.

Further, herein the 5-fluorouracil is synthesized by the following route:

herein the raw material or active pharmaceutical ingredient in the first aspect is provided by this refining method.

A third aspect of the present disclosure provides a 5-fluorouracil active pharmaceutical ingredient or composition, herein the 5-fluorouracil is prepared by the synthesis method of a method I and the refining method of a method II in the second aspect.

The synthesis method of the method I includes the following steps:

(1) condensation reaction: methyl fluoroacetate is used as a raw material, and condensed with ethyl formate in an organic solvent of sodium methoxide to obtain a fluoroformyl acetate enol sodium salt;

(2) cyclization reaction: the fluoroformyl acetate enol sodium salt obtained in the step (1) is cyclized with O-methylisourea sulfate to obtain 2-methoxy-5-fluorouracil; and (3) hydrolysis reaction: the 2-methoxy-5-fluorouracil obtained in the step (2) is hydrolyzed into 5-fluorouracil in a dilute hydrochloric acid.

The refining method of the method II includes the following steps:

(i) the first step is heating and dissolving, dissolving 5-fluorouracil in an organic solvent, heating and stirring until dissolved;

(ii) the second step is cooling and crystallizing, naturally cooling filtrate until a crystal is precipitated; and (iii) the third step is filtering and drying, filtering, washing a filter cake by using water, and draining and drying under a reduced pressure.

Preferably, the organic solvent in the step (i) is dimethylsulfoxide.

Preferably, the mass ratio of the 5-fluorouracil to the dimethylsulfoxide in the step (i) is 1:2-6, preferably 1:2.75-5.5, and further preferably 1:3.3.

Preferably, the heating and dissolving temperature in the step (i) is 45° C.-80° C.

Preferably, the cooling and crystallizing temperature in the step (ii) is 5-15° C., and the crystallizing time is 5-12 hours.

The beneficial effects of the present disclosure are as follows: by adopting this new-type purification method, the impurities in the production process are effectively removed, and in the case that it is guaranteed that the yield is higher than 70%, the purity of the 5-fluorouracil is higher than 99.98%, the content of the 5-methoxyuracil impurity (impurity D) is controlled below 0.01%, and the content of the single impurity is below 0.01%. Compared with an existing disclosed technology, the purification method provided by the present disclosure is high in product yield, fewer in purification times, and good in decolorization effect, and more importantly, the single impurity may be completely removed or less than 0.01%, the content of the impurities thereof is lower than the standards of Chinese Pharmacopoeia, and even lower than the standards of European Pharmacopoeia. This technology of purifying the 5-fluorouracil is in a world leading standard.

DETAILED DESCRIPTION OF THE PREFERRED EMBODIMENT

Figure 1:
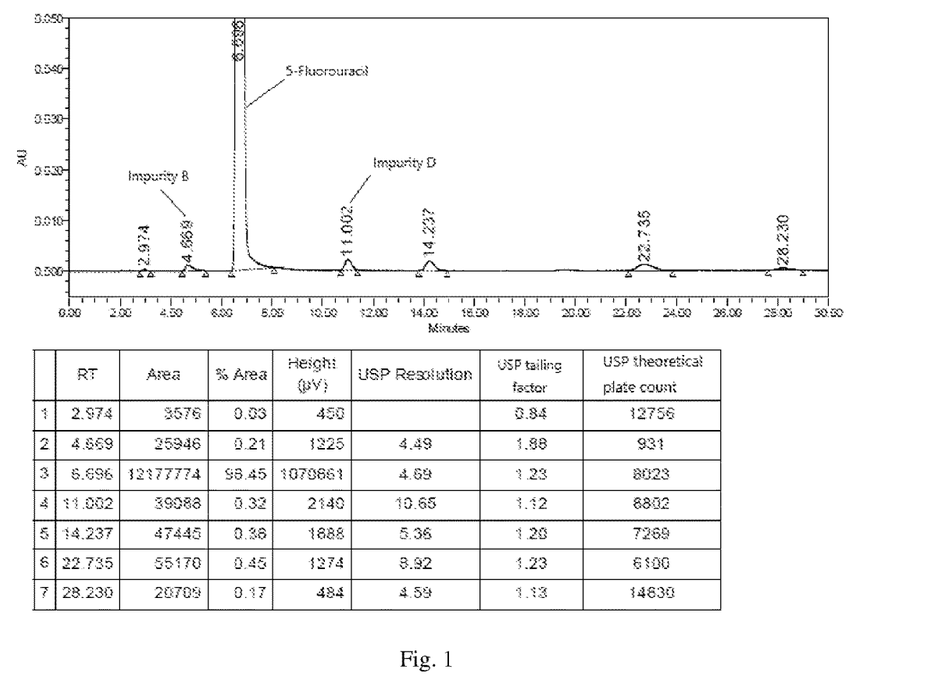
FIG. 1 is a High Performance Liquid Chromatography (HPLC) diagram of crude product 5-fluorouracil and a chromatogram of Embodiment 1.
Figure 2:
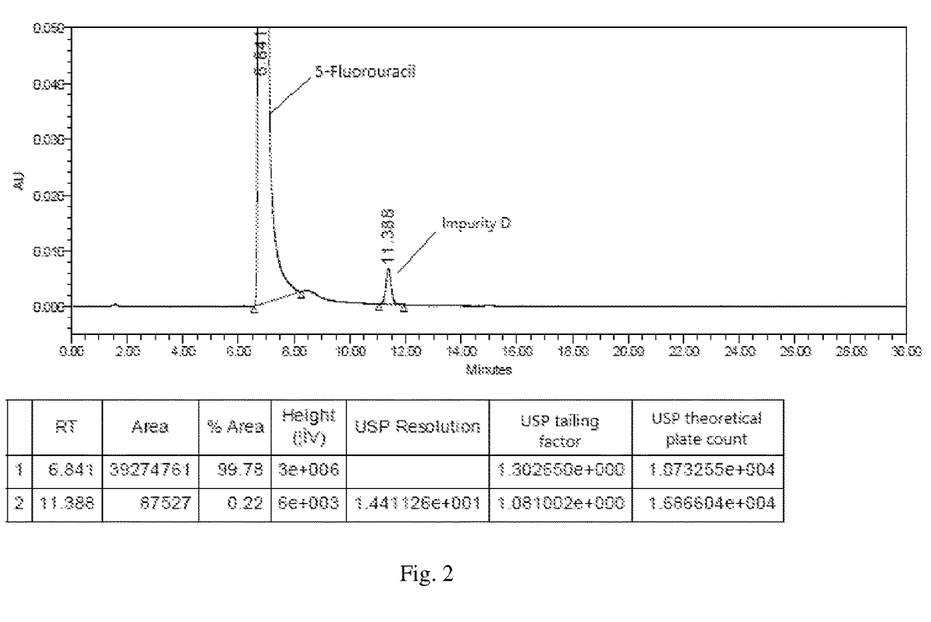
FIG. 2 is an HPLC diagram after the crude product 5-fluorouracil is refined by using methanol and water and a chromatogram of Embodiment 2.1.
Figure 3:
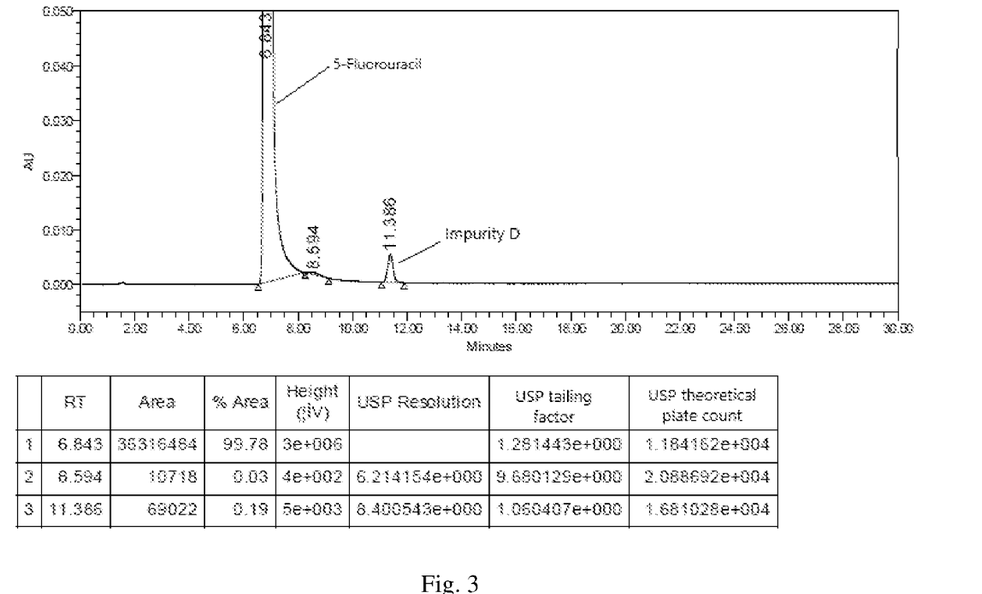
FIG. 3 is an HPLC diagram after the crude product 5-fluorouracil is refined by using 96% ethanol and water and a chromatogram of Embodiment 2.2.
Figure 4:
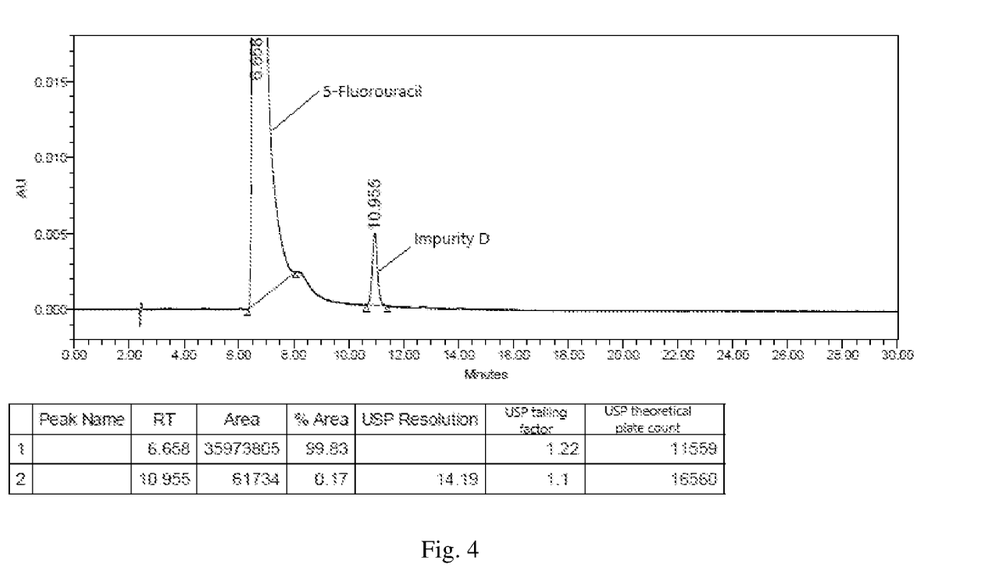
FIG. 4 is an HPLC diagram after the crude product 5-fluorouracil is refined by using isopropanol and water and a chromatogram of Embodiment 2.5.
Figure 5:
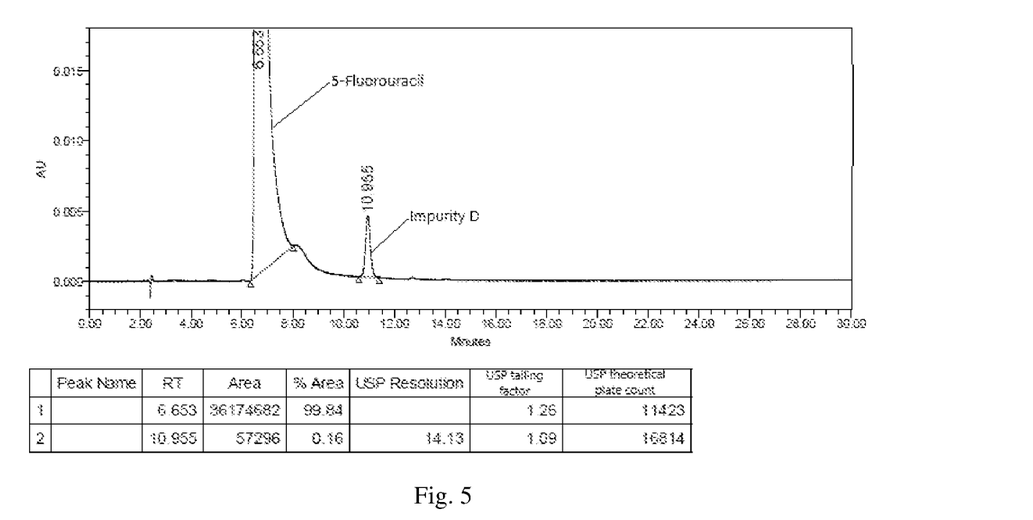
FIG. 5 is an HPLC diagram after the crude product 5-fluorouracil is refined by using acetone and water and a chromatogram of Embodiment 2.6.
Figure 6:
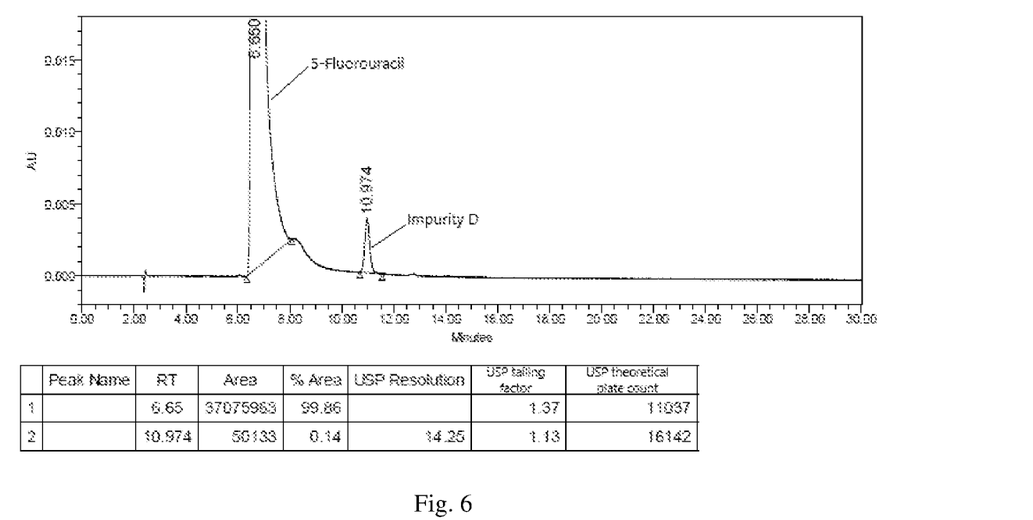
FIG. 6 is an HPLC diagram after the crude product 5-fluorouracil is refined by using n-butanol and water and a chromatogram of Embodiment 2.7.
Figure 7:
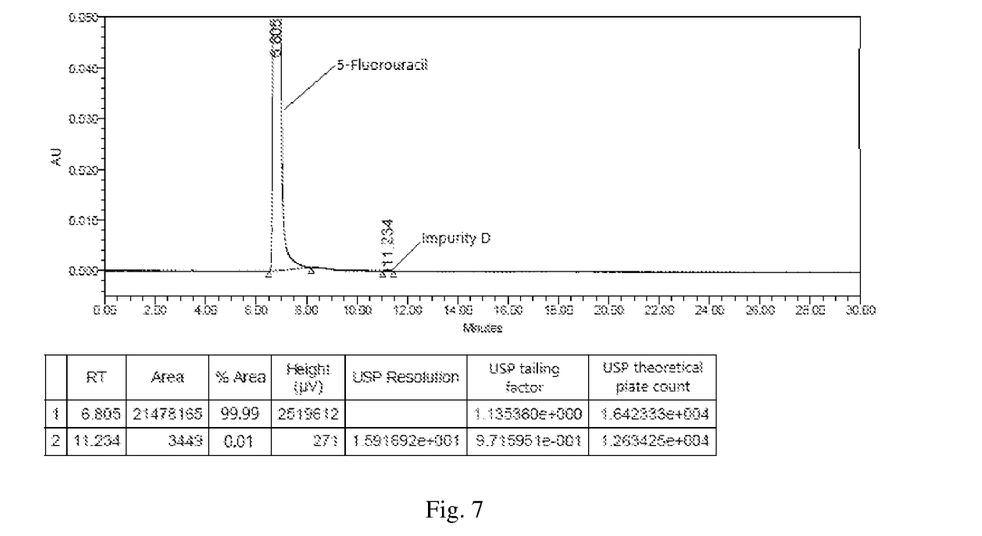
FIG. 7 is a chromatogram of Embodiment 2.10.
Figure 8:
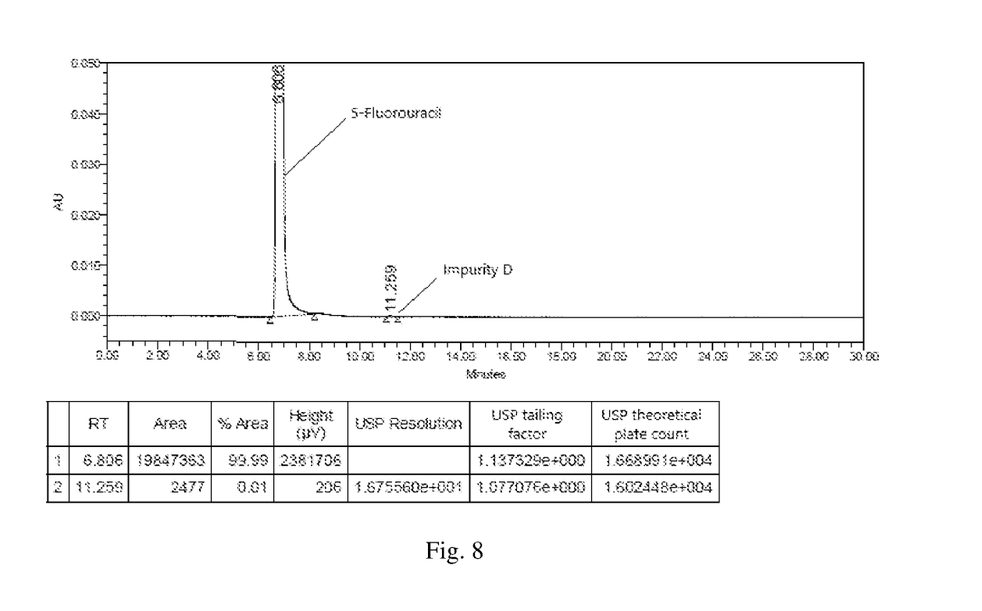
FIG. 8 is a chromatogram of Embodiment 2.11.
Figure 9:
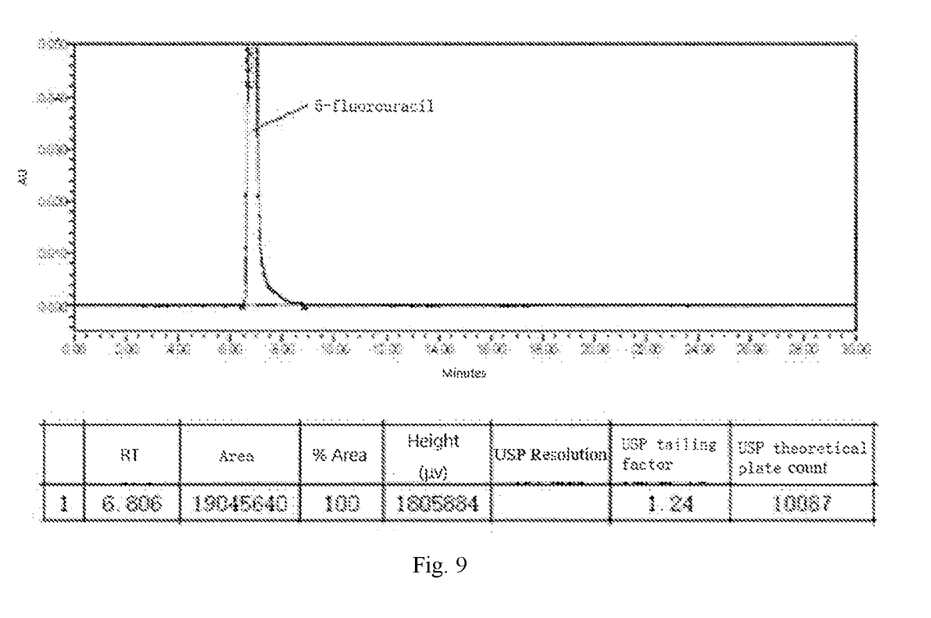
FIG. 9 is a chromatogram of Embodiment 2.12.

Term Definition:

Pharmaceutical composition: is a preparation containing 5-fluorouracil as an active ingredient in a form suitable for administration to a subject.

The present disclosure is further described in detail below with reference to specific embodiments. The description is for better understanding of the present disclosure, but does not limit the present disclosure.

Embodiment 1: Synthesis of 5-fluorouracil

The synthesis of 5-fluorouracil was synthesized according to a conventional method known in literatures; and its specific synthesis steps and routes were as follows:

Condensation Reaction:

In a dry reaction kettle, cold saline was put into a jacket, the temperature was lowered below 25° C. of an inner temperature, and 700 kg of toluene was put into it. A feeding hole was opened and 224 kg of a solid sodium methoxide was put into it, the feeding hole was closed, a stirrer was opened, and an emptying valve was opened. 420 kg of ethyl formate was pumped into an ethyl formate metering tank, the cold saline was put into the reaction kettle jacket, and cooled to 10-15° C. of the inner temperature, the ethyl formate was slowly dropwise added, the inner temperature was controlled to 10-20° C., and it took about 3-4 hours to drip 200 kg of methyl fluoroacetate was pumped into a methyl fluoroacetate metering tank, it was cooled with the cold saline to 8-15° C. of the inner temperature, the methyl fluoroacetate was dropwise added, and the inner temperature was kept within 25° C. during the dropwise addition. After the dropwise addition, the inner temperature was controlled at about 40° C., and it was reacted for about 20 hours until the reaction was completed.

Cyclization Reaction:

The above reaction solution was cooled to 20° C. of an inner temperature, 390 kg of sodium methoxide methanol solution and 400 kg of O-methyl isourea sulfate were slowly added successively under stirring, the stirring was continuously performed, and the inner temperature was kept at about 40 degrees for about 6 hours, until the reaction was completed. The reaction solution was transferred into a dissolving stratification pot, 500 kg of water and 60 kg of a dilute hydrochloric acid were added, and after standing, a lower water layer was transferred to a one-time acidification desolvation pot. Under the stirring, a hydrochloric acid was slowly added, and the inner temperature was kept below 35° C. It was neutralized to pH 5-6, and concentrated under a reduced pressure until effluent was apparently reduced, 1000 kg of the water and the dilute hydrochloric acid were added again, PH was adjusted to 2-3, and suction filtration was performed to obtain a crude product. The crude product was dissolved in 1000 kg of the water, it was stirred and heated to 90-100° C. of the inner temperature, and after the temperature was kept for 30 minutes, it was cooled to 40° C. of the inner temperature, feed liquid was pumped into a centrifugal machine. After being centrifuged, a yellow cyclic compound 5-methoxy fluorouracil (221.7 kg, and 81.63% of the yield) was obtained.

Hydrolysis Reaction:

90 kg of the yellow cyclic compound obtained above was taken, 198 kg of a concentrated hydrochloric acid was added, and it was reacted at a temperature of 55° C. for 3 hours until the reaction was completed. After the reaction was completed, it was cooled with cold saline to 5-15° C. of an inner temperature, feed liquid was transferred into the centrifugal machine, centrifuged, and water-washed until pH 5-6, and it was dried, to obtain a crude product 5-fluorouracil (65.24 kg, 80.3% of the yield, and 98.45% of the HPLC purity).

Its synthetic route was as follows:

Refining Process

Embodiment 2.1

5 g of a 5-fluorouracil crude product was added to mixed solution of 50 ml of methanol and 50 ml of water, the temperature was risen to 55° C.-60° C., stirring was performed until a solid was completely dissolved, the stirring was stopped, it was slowly cooled between 5° C. and 15° C., it was standing for 12 hours, filtering was performed, and a filter cake was washed with water, it was weighed after vacuum drying, to obtain 3.3 g of a 5-fluorouracil refined product. The yield was 66%, and the HPLC purity was 99.78%.

Embodiment 2.2

5 g of a 5-fluorouracil crude product was added to mixed solution of 50 ml of 95% ethanol and 30 ml of water, the temperature was risen to 55° C.-60° C., stirring was performed until a solid was completely dissolved, the stirring was stopped, it was slowly cooled between 5° C. and 15° C., it was standing for 12 hours, filtering was performed, and a filter cake was washed with water, it was weighed after vacuum drying, to obtain 3.7 g of a 5-fluorouracil refined product. The yield was 74%, and the HPLC purity was 99.78%.

Embodiment 2.3

5 g of a 5-fluorouracil crude product was added to mixed solution of 50 ml of acetonitrile and 30 ml of water, the temperature was risen to 55° C.-60° C., stirring was performed until a solid was completely dissolved, the stirring was stopped, it was slowly cooled between 5° C. and 15° C., it was standing for 12 hours, filtering was performed, and a filter cake was washed with water, it was weighed after vacuum drying, to obtain 2.5 g of a 5-fluorouracil refined product. The yield was 50%, and the HPLC purity was 99.78%.

Embodiment 2.4

5 g of a 5-fluorouracil crude product was added to mixed solution of 50 ml of tetrahydrofuran and 15 ml of water, the temperature was risen to 55° C.-60° C., stirring was performed until a solid was completely dissolved, the stirring was stopped, it was slowly cooled between 5° C. and 15° C., it was standing for 12 hours, filtering was performed, and a filter cake was washed with water, it was weighed after vacuum drying, to obtain 2.5 g of 5-fluorouracil. The yield was 50%, and the HPLC purity was 99.78%.

Embodiment 2.5

5 g of a 5-fluorouracil crude product was added to mixed solution of 50 ml of isopropanol and 20 ml of water, the temperature was risen to 55° C.-60° C., stirring was performed until a solid was completely dissolved, the stirring was stopped, it was slowly cooled between 5° C. and 15° C., it was standing for 12 hours, filtering was performed, and a filter cake was washed with water, it was weighed after vacuum drying, to obtain 3.5 g of 5-fluorouracil. The yield was 70%, and the HPLC purity was 99.83%.

Embodiment 2.6

5 g of a 5-fluorouracil crude product was added to mixed solution of 50 ml of acetone and 35 ml of water, the temperature was risen to 55° C.-60° C., stirring was performed until a solid was completely dissolved, the stirring was stopped, it was slowly cooled between 5° C. and 15° C., it was standing for 12 hours, filtering was performed, and a filter cake was washed with water, it was weighed after vacuum drying, to obtain 2.5 g of 5-fluorouracil. The yield was 50%, and the HPLC purity was 99.84%.

Embodiment 2.7

5 g of a 5-fluorouracil crude product was added to mixed solution of 50 ml of n-butanol and 35 ml of water, the temperature was risen to 55° C.-60° C., stirring was performed until a solid was completely dissolved, the stirring was stopped, it was slowly cooled between 5° C. and 15° C., it was standing for 12 hours, filtering was performed, and a filter cake was washed with water, it was weighed after vacuum drying, to obtain 4 g of 5-fluorouracil. The yield was 80%, and the HPLC purity was 99.86%.

Embodiment 2.8

10 g of a 5-fluorouracil crude product was dissolved in 110 mL of water, 1 g of activated carbon was added, the temperature was risen to 95-105° C., stirring and refluxing were performed for 3 hours, until 5-fluorouracil solids were all dissolved, and after it was filtered while hot, filtrate was standing, it was slowly cooled between 5° C. and 15° C., it was standing for 12 hours, filtering was performed, and a filter cake was washed with water, it was weighed after vacuum drying, to obtain 8.1 g of 5-fluorouracil. The yield was 81%, and the HPLC purity was 99.82%.

Embodiment 2.9

5 g of a 5-fluorouracil crude product was added to mixed solution of 25 mL of dimethyl formamide (DMF) and 20 mL of water, the temperature was risen to 95° C.-105° C., stirring was performed, until solids were all dissolved, the stirring was stopped, it was slowly cooled between 5° C. and 15° C., it was standing for 12 hours, filtering was performed, a filter cake was washed with water, and after drying, it was recrystallized twice with the DMF and water, to obtain 0.625 g of 5-fluorouracil. The yield was 12.5%, and the HPLC purity was 99.78%.

Embodiment 2.10

5 g of a 5-fluorouracil crude product was dissolved in 25 mL of dimethyl sulfoxide, the temperature was risen to 45° C.-50° C., stirring was performed, until solids were all dissolved, the stirring was stopped, it was slowly cooled between 5° C. and 15° C., it was standing for 12 hours, filtering was performed, a filter cake was washed with water, it was weighed after vacuum drying, to obtain 3.6 g of 5-fluorouracil. The yield was 72%, and the HPLC purity was 99.99%.

Embodiment 2.11

10 g of a 5-fluorouracil crude product was dissolved in 25 mL of dimethyl sulfoxide, the temperature was risen to 45° C.-50° C., stirring was performed, until solids were all dissolved, the stirring was stopped, it was slowly cooled between 5° C. and 15° C., it was standing for 12 hours, filtering was performed, a filter cake was washed with water, it was weighed after vacuum drying, to obtain 7.5 g of 5-fluorouracil. The yield was 75%, and the HPLC purity was 99.99%.

Embodiment 2.12

60 g of a 5-fluorouracil crude product was dissolved in 180 mL of dimethyl sulfoxide, the temperature was risen to 70° C.-80° C., stirring was performed, until solids were all dissolved, the stirring was stopped, it was slowly cooled between 5° C. and 15° C., it was standing for 12 hours, filtering was performed, a filter cake was washed with water, it was weighed after vacuum drying, to obtain 47.4 g of 5-fluorouracil. The yield was 79%, and the HPLC purity was 100.00%.

Herein the detection conditions of the above-mentioned HPLC may be according to those disclosed in the pharmacopoeia or the conditions well-known to those skilled in the art:

Chromatographic column: Waters, SPHERISORB ODS-2, 4.6×250 mm, 5 μm;

Mobile phase: 6.805 g/L of potassium dihydrogen phosphate aqueous solution (6.805 g of potassium dihydrogen phosphate was taken and dissolved in 1000 ml of water, and pH was adjusted to 5.7±0.1 with 5 M potassium hydroxide);

Detection wavelength: 266 nm, and Flow rate: 1.0 ml/min;

Column temperature: 30° C., sample injection at the room temperature, and Injection volume: 20 ul; and Collection time: 30 min.

The process parameters, the yield, the purity, and the contents of the impurity B and the impurity D of the above Embodiment 1 and Embodiments 2.1-2.12 were as shown in Table 1.

TABLE 1

Comparative data of refining effects of 5-fluorouracil

| Embodiment number | Batch | Process (key parameters) | Yield | Impurity B | Impurity D | API purity |
|---|---|---|---|---|---|---|
| Embodiment 1 | | | | 0.21% | 0.32% | 98.45% |
| Embodiment 2.1 | 5 g | Methanol 50 ml Water 50 ml Temperature 55-60° C. | 66% | / | 0.22% | 99.78% |
| Embodiment 2.2 | 5 g | 95% ethanol 50 ml Water 30 ml Temperature 55-60° C. | 74% | / | 0.19% | 99.78% |
| Embodiment 2.3 | 5 g | Acetonitrile 50 ml Water 30 ml Temperature 55-60° C. | 50% | 0.02% | 0.20% | 99.78% |
| Embodiment 2.4 | 5 g | Tetrahydrofuran 50 ml Water 15 ml Temperature 55-60° C. | 50% | 0.01% | 0.21% | 99.78% |
| Embodiment 2.5 | 5 g | Isopropanol 50 ml Water 20 ml Temperature 55-60° C. | 70% | / | 0.17% | 99.83% |
| Embodiment 2.6 | 5 g | Acetone 50 ml Water 35 ml Temperature 55-60° C. | 50% | / | 0.16% | 99.84% |
| Embodiment 2.7 | 5 g | N-butanol 50 ml Water 35 ml Temperature 55-60° C. | 80% | / | 0.14% | 99.86% |
| Embodiment 2.8 | 10 g | Water 110 ml Activated carbon 1 g Temperature 95-105° C. | 81% | / | 0.18% | 99.82% |

TABLE 1-continued

Comparative data of refining effects of 5-fluorouracil

| Embodiment number | Batch | Process (key parameters) | Yield | Impurity B | Impurity D | API purity |
|---|---|---|---|---|---|---|
| Embodiment 2.9 | 5 | DMF 25 mL Water 20 mL 95° C.-105° C.; crystallized for three times | 12.5% | / | 0.21% | 99.79% |
| Embodiment 2.10 | 5 g | Dimethylsulfoxide 25 ml Temperature 45-50° C. | 72% | / | 0.01% | 99.99% |
| Embodiment 2.11 | 10 g | Dimethylsulfoxide 25 ml Temperature 45-50° C. | 75% | / | 0.01% | 99.99% |
| Embodiment 2.12 | 60 g | Dimethylsulfoxide 180 ml Temperature 70-80° C. | 79% | / | / | 100.00% |

Embodiment 3-1: Injection of 5-fluorouracil

Ingredient:
5-fluorouracil: 200 g, obtained by purification according to the method of Embodiment 2.10
Sodium hydroxide: 60 g
Edetate disodium: 0.1 g
Adding water for injection to: 10000 mL
Preparation Method:
Water which was more than 50% of a total volume of a composition was mixed with fluorouracil, after it was prepared into 10% of solution by using a sodium hydroxide, a pH value of the above solution was adjusted to be greater than 8, and after being all dissolved, an edetate disodium dissolved in a small amount of water was added, and then 0.3% medicinal charcoal was weighed and added into a container, stirring was performed, decarbonizing and filtering were performed, the water was supplemented to a full amount, and it was stirred evenly.

Embodiment 3-2: Freeze-Dried Powder of 5-Fluorouracil Composition

Ingredient and matching ratio: 9.26-11.16 parts of 5-fluorouracil, 4.63-5.58 parts of chitosan nanoparticles, and 84.35-88.56 parts of water for injection, herein the 5-fluorouracil was obtained by purification according to the method of Embodiment 2.11.

Embodiment 3-3: Oral Emulsion of 5-Fluorouracil

Ingredient and matching ratio: the 5-fluorouracil accounts for 1-5% of a total weight of oral emulsion, other auxiliary materials account for 20-40% of the total weight of the oral emulsion, purified water accounts for 60-80% of the total weight of the oral emulsion, and the auxiliary materials were one or more of soybean lecithin, vegetable oil, sodium hydroxide, ethylparaben, and orange essence, herein the 5-fluorouracil was obtained by purification according to the method of Embodiment 2.12.

It is apparent to those skilled in the art that various modifications and variations may be made in the present disclosure without departing from the spirit and scope of the present disclosure. Thus, if these modifications and variations of the present disclosure fall within scopes of the claims of the present disclosure and equivalent technologies thereof, the present disclosure is also intended to include these modifications and variations.

What is claimed is:
1. A 5-fluorouracil raw material or active pharmaceutical ingredient, comprising 5-fluorouracil with a weight percentage of 99.9% or more and impurities with a weight percentage of 0.05% or less, and the impurities are selected from 5-methoxyuracil, and dihydropyrimidine-2,4,5(3H)-trione;
wherein the structure of the 5-methoxyuracil is

(D)

and
the structure of the dihydropyrimidine-2,4,5(3H)-trione is (B)

2. A composition comprising the 5-fluorouracil raw material or active pharmaceutical ingredient according to claim 1.
3. A refining method for high-purity 5-fluorouracil, comprising the following steps:
(i) the first step is heating and dissolving, dissolving 5-fluorouracil in an organic solvent, heating and stirring until dissolved;

(ii) the second step is cooling and crystallizing, naturally cooling filtrate until a crystal is precipitated; and
(iii) the third step is filtering and drying, filtering, washing a filter cake by using a polar solvent, and draining and drying under a reduced pressure,
wherein the organic solvent in the step (i) is dimethylsulfoxide.

4. The refining method according to claim 3, wherein the mass ratio of the 5-fluorouracil to the dimethylsulfoxide in the step (i) is 1:2-6.

5. The refining method according to claim 3, wherein the heating and dissolving temperature in the step (i) is 45° C.-80° C.

6. The refining method according to claim 3, wherein the cooling and crystallizing temperature in the step (ii) is 5-15° C., and the crystallizing time is 5-12 hours.

7. The refining method according to claim 3, wherein the polar solvent in the step (iii) is selected from water.

8. The refining method according to claim 3, wherein impurities further removed by the refining method comprise: dihydropyrimidine-2,4,5(3H)-trione and/or 5-methoxyuracil.

9. The refining method according to claim 3, wherein the 5-fluorouracil is synthesized by a method I, and the method I comprises the following steps:
(1) condensation reaction: methyl fluoroacetate is used as a raw material, and condensed with ethyl formate in an organic solvent of sodium methoxide to obtain a fluoroformyl acetate enol sodium salt;
(2) cyclization reaction: the fluoroformyl acetate enol sodium salt obtained in the step (1) is cyclized with O-methylisourea sulfate to obtain 2-methoxy-5-fluorouracil; and
(3) hydrolysis reaction: the 2-methoxy-5-fluorouracil obtained in the step (2) is hydrolyzed into 5-fluorouracil in a dilute hydrochloric acid.

10. The 5-fluorouracil raw material or active pharmaceutical ingredient according to claim 1, wherein the 5-fluorouracil has a weight percentage of 99.99% or more and the impurities have a weight percentage of 0.01% or less.

11. The refining method according to claim 4, wherein the mass ratio of the 5-fluorouracil to the dimethylsulfoxide in the step (i) is 1:2.75-5.5.

12. The refining method according to claim 11, wherein the mass ratio of the 5-fluorouracil to the dimethylsulfoxide in the step (i) is 1:3.3.

13. The 5-fluorouracil raw material or active pharmaceutical ingredient according to claim 1, wherein the 5-fluorouracil raw material or active pharmaceutical ingredient is prepared by a refining method comprising the following steps:
(i) the first step is heating and dissolving, dissolving 5-fluorouracil in an organic solvent, heating and stirring until dissolved;
(ii) the second step is cooling and crystallizing, naturally cooling filtrate until a crystal is precipitated; and
(iii) the third step is filtering and drying, filtering, washing a filter cake by using a polar solvent, and draining and drying under a reduced pressure;
wherein the organic solvent in the step (i) is dimethylsulfoxide.

* * * * *